US012383373B2

(12) United States Patent
VanDerWoude et al.

(10) Patent No.: US 12,383,373 B2
(45) Date of Patent: Aug. 12, 2025

(54) SURGICAL SPONGES AND INSTRUMENT DETECTION DURING A SURGICAL PROCEDURE

(71) Applicant: Stryker Corporation, Kalamazoo, MI (US)

(72) Inventors: Brian James VanDerWoude, Portage, MI (US); Justin Andrews, Schoolcraft, MI (US)

(73) Assignee: Stryker Corporation, Portage, MI (US)

( * ) Notice: Subject to any disclaimer, the term of this patent is extended or adjusted under 35 U.S.C. 154(b) by 247 days.

(21) Appl. No.: 17/776,458

(22) PCT Filed: Nov. 13, 2020

(86) PCT No.: PCT/US2020/060399
§ 371 (c)(1),
(2) Date: May 12, 2022

(87) PCT Pub. No.: WO2021/097197
PCT Pub. Date: May 20, 2021

(65) Prior Publication Data
US 2022/0387134 A1 Dec. 8, 2022

Related U.S. Application Data

(60) Provisional application No. 62/934,795, filed on Nov. 13, 2019.

(51) Int. Cl.
*H04Q 5/22* (2006.01)
*A61B 90/98* (2016.01)
(Continued)

(52) U.S. Cl.
CPC .......... *A61B 90/98* (2016.02); *G06K 7/10386* (2013.01); *G06K 19/0723* (2013.01);
(Continued)

(58) Field of Classification Search
CPC ............ A61B 90/98; A61B 2090/0805; A61B 2560/0431; H04W 4/80; G06K 7/10386; G06K 19/0723
See application file for complete search history.

(56) References Cited

U.S. PATENT DOCUMENTS 6,412,700 B1 * 7/2002 Blake ................... G02B 26/106
235/472.01
7,703,674 B2 4/2010 Stewart et al.
(Continued)

FOREIGN PATENT DOCUMENTS

WO 2017112051 A1 6/2017
WO WO-2018132527 A1 * 7/2018 ........... G06F 16/538
(Continued)

OTHER PUBLICATIONS

International Search Report for Application No. PCT/US2020/060399 dated Feb. 18, 2021, 3 pages.
(Continued)

*Primary Examiner* — Quang Pham
(74) *Attorney, Agent, or Firm* — Howard & Howard Attorneys PLLC

(57) ABSTRACT

System and method of managing one or more surgical articles, wherein the surgical article can include a surgical sponge comprising an identification element, and wherein managing can include counting, locating, or both. The identification element can be a RFID tag. The RFID tag stores unique identification information relative to the surgical sponge. The system and method for detecting RFID tags may include a hand-held RFID reader operable in a first count-in mode and in a second count-out mode; the hand-held RFID reader may be receivable in a cradle that can determine the presence of the hand-held RFID reader in the cradle; and where operation of the hand-held RFID reader in the second count-out mode is enabled when the hand-held
(Continued)

RFID reader is present in the cradle and the second count-out mode is disabled when the hand-held RFID reader is absent from the cradle.

20 Claims, 7 Drawing Sheets

(51) Int. Cl.
G06K 7/10 (2006.01)
G06K 19/07 (2006.01)
H04W 4/80 (2018.01)
A61B 90/00 (2016.01)

(52) U.S. Cl.
CPC ....... *H04W 4/80* (2018.02); *A61B 2090/0805* (2016.02); *A61B 2560/0431* (2013.01)

(56) References Cited

U.S. PATENT DOCUMENTS

| | | | |
|---|---|---|---|
| 8,181,860 B2 | 5/2012 | Fleck et al. | |
| 8,186,597 B1* | 5/2012 | Fletcher | G06K 7/10881 |
| | | | 235/462.43 |
| 8,985,446 B2 | 3/2015 | Fleck et al. | |
| 9,414,973 B2 | 8/2016 | Fleck et al. | |
| 9,530,036 B2 | 12/2016 | Fleck et al. | |
| 9,672,397 B2 | 6/2017 | Fleck et al. | |
| 9,974,625 B2 | 5/2018 | Fleck et al. | |
| 10,529,015 B1* | 1/2020 | Hill | G06Q 20/4014 |
| 10,729,510 B2 | 8/2020 | Fleck et al. | |
| 11,090,129 B2 | 8/2021 | Fleck et al. | |
| 11,116,598 B1 | 9/2021 | Fleck et al. | |
| 2009/0295541 A1* | 12/2009 | Roof | G06K 7/10386 |
| | | | 340/10.1 |
| 2009/0321525 A1* | 12/2009 | Barkan | G06K 7/109 |
| | | | 235/472.01 |
| 2011/0073658 A1* | 3/2011 | Vassura | G06K 7/10881 |
| | | | 235/472.01 |
| 2012/0077433 A1* | 3/2012 | Walker | H04M 1/72412 |
| | | | 455/41.1 |
| 2012/0265623 A1* | 10/2012 | Zhu | G06K 7/1095 |
| | | | 705/16 |
| 2012/0305650 A1* | 12/2012 | Prpa | A61B 90/90 |
| | | | 235/470 |
| 2013/0123616 A1* | 5/2013 | Merritt | G06F 3/04883 |
| | | | 600/463 |
| 2013/0344804 A1* | 12/2013 | Chen | H04B 5/48 |
| | | | 455/41.1 |
| 2014/0259557 A1* | 9/2014 | Egan | A61B 50/20 |
| | | | 24/335 |
| 2014/0375422 A1* | 12/2014 | Huber | G07C 9/00571 |
| | | | 340/5.61 |
| 2015/0081067 A1* | 3/2015 | Yeh | G09B 19/0038 |
| | | | 700/94 |
| 2015/0097701 A1* | 4/2015 | Al-Ali | A61M 16/0051 |
| | | | 340/870.07 |
| 2015/0216610 A1 | 8/2015 | Augustine | |
| 2016/0030613 A1* | 2/2016 | Paul | A61B 5/14532 |
| | | | 250/455.11 |
| 2016/0073972 A1* | 3/2016 | Alpert | A61B 5/7425 |
| | | | 600/486 |
| 2016/0188925 A1* | 6/2016 | Liu | G06K 7/10316 |
| | | | 340/10.34 |
| 2016/0292560 A1* | 10/2016 | Ayatollahi | G06K 19/0726 |
| 2017/0119252 A1* | 5/2017 | Kim | A61B 5/0024 |
| 2017/0163788 A1* | 6/2017 | Andersen | H04N 7/142 |
| 2017/0296301 A1* | 10/2017 | Dor | A61B 34/20 |
| 2018/0285704 A1* | 10/2018 | Stewart | G06Q 10/00 |
| 2018/0344429 A1 | 12/2018 | Stewart | |
| 2019/0000589 A1 | 1/2019 | Vanderwoude et al. | |
| 2019/0087544 A1* | 3/2019 | Peterson | G16H 50/20 |
| 2019/0311802 A1* | 10/2019 | Kokubo | A61B 90/70 |
| 2021/0068907 A1* | 3/2021 | Fuerst | A61B 90/361 |
| 2021/0085428 A1 | 3/2021 | Yavari et al. | |
| 2021/0369387 A1 | 12/2021 | Fleck et al. | |
| 2023/0316028 A1* | 10/2023 | Stewart | G06K 17/00 |
| | | | 340/539.32 |

FOREIGN PATENT DOCUMENTS

| | | |
|---|---|---|
| WO | 2019028334 A2 | 2/2019 |
| WO | 2021041795 A1 | 3/2021 |

OTHER PUBLICATIONS

Youtube, "Stryker SurgiCount Surgical Tablet Video", https://www.youtube.com/watch?v=gml6drYiNgs, Sep. 11, 2020, 3 Pages.

* cited by examiner

SURGICAL SPONGES AND INSTRUMENT DETECTION DURING A SURGICAL PROCEDURE

REFERENCE TO RELATED APPLICATION

This application is a national phase filing of International Application No. PCT/US2020/060399, filed Nov. 13, 2020, which claims priority to and all the benefits of U.S. Provisional Patent Application No. 62/934,795, filed Nov. 13, 2019, the entire contents of which are hereby incorporated by reference.

SUGGESTED CLASSIFICATION

A61B2090/0804: A human necessity in medical sciences used in surgery as an accessory for detecting and counting instruments used in surgery.

BACKGROUND

Before and after a surgical procedure, it is important to track the tools and surgical articles utilized during the procedure to ensure proper sterilization and disposal of the tools or articles. It is also important to have an accurate count of the tools or articles to ensure that none of the tools or articles were inadvertently lost or retained inside a patient. A surgical sponge is an example of a surgical article, which may be comprised of absorbent material for soaking up blood and other bodily fluids in and around an incision site. Health care professionals (HCPs) typically follow strict procedures to account for each and every sponge used during a surgery, in view of the risks associated with a surgical sponge being inadvertently retained inside a patient.

In the past, HCPs have relied upon counting surgical sponges by hand, however, manual counting requires handling of and exposure to soiled sponges and is prone to human error. To reduce the potential for retained surgical sponges associated with inaccurate manual counting methods, surgical sponges have been tagged with radio-opaque markers, barcodes, or wireless transponders, such as RFID or LC respondent transponders. Therefore, there is a need to provide for efficient and accurate counting of the surgical sponges to reduce or eliminate the risks associated with surgical articles being retained inside a patient.

SUMMARY

A surgical article system for proper removal of surgical articles following a surgical procedure is provided. The surgical articles include an identification tag comprising identification information identifying the surgical article. The system includes a hand-held reader operable to read the identification information from the identification tag. The system includes a cradle, where the cradle is adapted to receive the hand-held reader. The system includes a set of instructions stored in a non-transitory computer readable memory. The set of instructions, when executed, cause the system to selectively operate the hand-held reader in a first count-in mode wherein the system stores information, based on the identification information, identifying the surgical article as counted-in for use in the surgical procedure. The set of instructions, when executed, also cause the system to selectively operate the hand-held reader in a second count-out mode wherein the system stores information, based on the identification information, identifying the surgical article as counted-out and removed from the surgical procedure. The cradle is operable to determine a presence of the hand-held reader received in the cradle. The system enables operation of the hand-held reader in the second count-out mode based on the presence of the hand-held reader received in the cradle.

The surgical article used in the system may be a surgical sponge. The hand-held reader may include an RFID reader and wherein the identification tag comprises an RFID tag. The hand-held reader may include a processor and the non-transitory memory storing the set of instructions. The reader may further include a display device and an input device. The set of instructions, when executed, may further cause the system to display on the display device a status of the hand-held reader selectively operated in the first count-in mode or the second count-out mode. The set of instructions, when executed, may further cause the system to display information selected from among the article identification information, a count of surgical articles identified as counted-in, a count of surgical articles identified as counted-out, and combinations thereof.

The system may include a base unit in electronic communication with the hand-held reader. The base unit may include a processor. The base unit may include the non-transitory memory storing the set of instructions, a display device, and an input device. The set of instructions, when executed, may cause the system to display on the display device a status of the reader selectively operated in the first count-in mode or the second count-out mode. The set of instructions, when executed, may cause the system to display information selected from among the article identification information, a count of surgical articles identified as counted-in, a count of surgical articles identified as counted-out, and combinations thereof. The base unit may be a tablet computing device, and the input device is a touchscreen of the tablet computing device.

The system may include a mobile pedestal stand having a pole. The base unit and the cradle may be supported on the pole. The pedestal stand may be arranged to be disposed outside a sterile field of the surgical procedure.

The cradle may include a switch so that the reader, when received by the cradle, actuates the switch. The cradle may determine the presence of the reader received in the cradle based on the actuation of the switch. The cradle may be operable to determine a presence of the reader via near field communication between the cradle and reader. The near field communication between the cradle and the hand-held reader may require a proximity between the cradle and hand-held reader that is present only when the reader is received in the cradle. The cradle may be operable to determine a presence of the reader repeatedly while the system is selectively operating the reader in the second count-out mode. The set of instructions, when executed, may cause the system to trigger an alert and terminate operating the reader in the second count-out mode based on the cradle determining the reader is not present in the cradle.

The system including the base unit may be in electronic communication with the hand-held reader via a Bluetooth communication protocol. The Bluetooth pairing between the base unit and the hand-held reader may be based on information communicated via the near field communication between the hand-held reader and the cradle.

A method for ensuring proper removal of surgical articles following a surgical procedure is provided. The surgical articles include an identification tag that includes identification information identifying the surgical article. The method includes operating a hand-held reader in a first count-in mode including storing information identifying the surgical article as counted-in for use in the surgical procedure. The method includes operating the hand-held reader in a second count-out mode including storing information identifying the surgical article as counted-out and removed from the surgical procedure. The method includes receiving the hand-held reader in a cradle. The cradle is operable to determine a presence of the reader received in the cradle. The method includes determining a presence or absence of the reader in the cradle. In the method, operating the hand-held reader in the second count-out mode is based on the hand-held reader being present in the cradle. The cradle may be operable to determine a presence of the hand-held reader via near field communication between the cradle and hand-held reader.

The method may include selecting, on a base unit, from among the first count-in mode and the second count-out mode for the hand-held reader operation, wherein the base unit is in electronic communication with the cradle and the base unit is in electronic communication with the hand-held reader via a Bluetooth communication protocol. The method may include pairing the hand-held reader with the base unit for Bluetooth communication. The Bluetooth pairing may be based on information communicated via near field communication between the hand-held reader and the cradle.

The method may include displaying, on a display device, a status of the hand-held reader as operating in the first count-in mode or the second count-out mode. The method may include displaying, on a display device, information selected from among the identification information, a count of surgical articles identified as counted-in, a count of surgical articles identified as counted-out, and combinations thereof.

BRIEF DESCRIPTION OF THE DRAWINGS

Referring now to the drawings, exemplary illustrations are shown in detail. Although the drawings represent schematic illustrations, the drawings are not necessarily to scale and certain features may be exaggerated to better illustrate and explain an innovative aspect of an illustrative example. Further, the exemplary illustrations described herein are not intended to be exhaustive or otherwise limiting or restricting to the precise form and configuration shown in the drawings and disclosed in the following detailed description.

Advantages of the present disclosure will be readily appreciated as the same becomes better understood by reference to the following detailed description when considered in connection with the accompanying drawings wherein.

DETAILED DESCRIPTION

The present disclosure relates to systems and methods for managing an inventory of surgical articles during a surgical procedure to ensure the proper removal of the surgical articles from the patient following the surgical procedure and thereby prevent the undesirable retention of the surgical articles within the patient.

Figure 1:
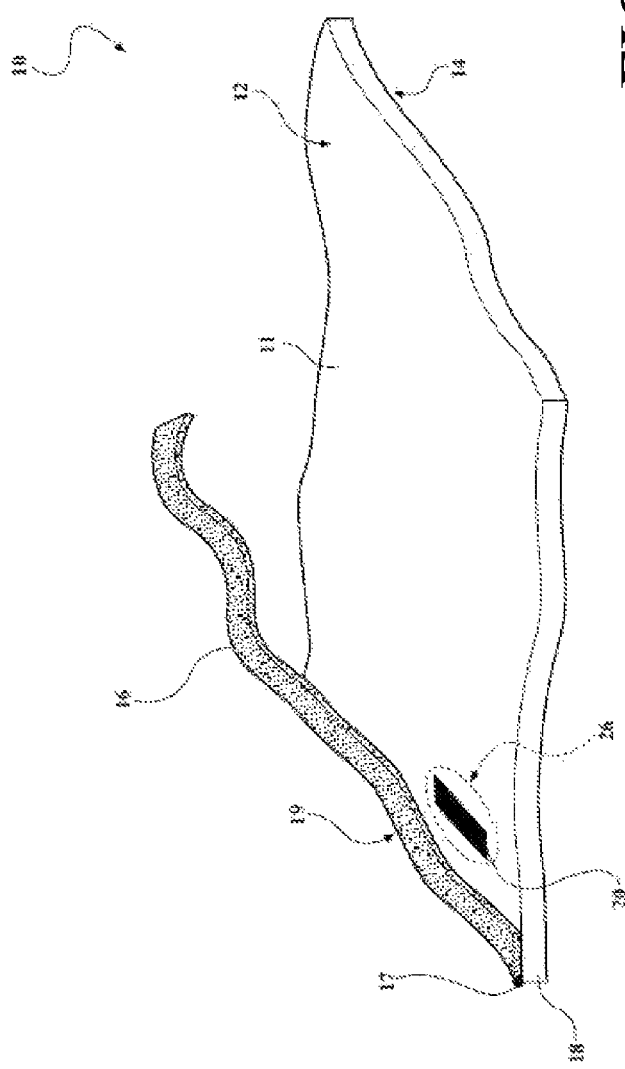
FIG. 1 illustrates a surgical article as a surgical sponge.

FIG. 1 illustrates one such surgical article, a surgical sponge 10, having one or more tags for counting or detecting the surgical article before, during, or after a surgical procedure. In particular, the surgical article illustrated in FIG. 1 may comprise a surgical sponge 10 further comprising a tag 20, as described in detail below. However, while not shown in the Figures, it has been contemplated that other alternatives of the surgical article 10 can include laparotomy pads, gauzes, implants, towels, suture needles, clips, staples, or surgical instruments. Another example of the surgical article may comprise a surgical instrument, such as a scalpel or forceps, comprising a tag 20.

The tag 20 may comprise counting element(s), detecting element(s), or any combination thereof and may be incorporated within handles, between layers of, or other portions of the surgical article 10. As described in detail below, each surgical article 10 can include one or more tags 20, and each tag 20 may include various combinations of the counting elements or the detecting elements. For example, one of these tags 20 may comprise an RFID element (RFID tag). However, each tag 20 can include any number of counting elements and any number of detecting elements, in addition or in the alternative, consistent with the disclosure herein.

The tag 20 may be configured to include unique identification information for each surgical article 10. The unique identification information may comprise a serial number or other identifier that is unique and assigned only to the corresponding article 10. The unique identification information may further convey the type, size, weight, manufacturing dates, expiration date, number of similar articles 10 in a corresponding package, the unique identification of the articles packaged together, or other information used for counting or detecting the article 10.

The tag 20 may convey the unique identification information by transmitting an electromagnetic signal or wave corresponding to the unique identification information. Each surgical article 10 may comprise, in addition, a second tag (not shown) having the unique identifier or other information in a form scannable by an optical-scanning device or human-readable that can be manually entered into a user interface of the scanning device, computer, or other system. A plurality of tags on a surgical article may be different from one another yet include the same unique identification information related to the specific surgical article to which the tag is affixed. The tag 20 may allow an HCP to identify the number of surgical articles 10 present or to determine a location of the surgical articles 10 within the body of the patient, within an operating room, or both inside the body of the patient and within the operating room. In other alternatives, the tag(s) 20 may be detectable within the operating room but not within the body of the patient.

The tag 20 may be incorporated within handles, between layers of, or other portions of the surgical article 10. For example, the tag 20 can be adhered to or encapsulated within the layers of the surgical article 10, embedded within the handle, or coupled to other portions of the article 10. The tag 20 may be encapsulated within layers of a polymer label adhered to the article 10. Each tag 20 may be rigid to increase its service life. In other examples, the tag 20 can be flexible to permit the surgical article 10 and the tag to be folded or otherwise shaped in a manner for use within a patient's body. Furthermore, the tag 20 may be encapsulated in a biocompatible plastic coating, pouch, or housing 26 that is water-impermeable and sterilizable. The housing 26 may be coupled to the surgical article 10 via stitching, adhesive, or similar type of fastener.

The counting or detecting elements of the tag 20 may be configured to cooperate with at least one detector-interrogating antenna (detecting antenna) of a reader, as a scanning device, such as a hand-held device manipulatable by the HCP. Although described as a hand-held device, or hand-held reader, this description is not intended to limit the operation of the device or reader to while the device or reader is being held by hand. Rather, this description conveys that the device or reader may be operated while being held by hand, and may also be operated while disposed in a static or stationary arrangement. This distinguishes the hand-held reader from one that is permanently mounted or stationary. Alternatively, a detector-interrogating antenna may be incorporated into a surgical instrument tray, surgical cart, or canister. However, it is contemplated that any suitable antenna, including one integrated within the optical-scanning device can be configured to detect the detecting element included in the tag 20. The antenna may further comprise a circuit, coil, or loop configured to define a plane of the antenna, wherein a signal, which can be carried on, or understood as, an electromagnetic field, may be transmitted outward from the plane of the antenna, to be received by the tags 20 which then provide a response signal that can be projected back to the antenna. The Applicant has described a scanning device or scanning apparatus with an antenna in U.S. Pat. No. 8,181,860, filed on Sep. 13, 2007, the disclosure of which is hereby incorporated by reference.

A wide variety of tags may be commercially available from various manufacturers. Certain tags may be configured to provide significant amounts of user accessible memory, sometimes in the form of read-only memory or write-once memory. One exemplary tag is an RFID tag 20 detectable by a RFID antenna. However, it is contemplated that the surgical article 10 can include any suitable tag detectable by any corresponding detecting antenna. The Applicant has described a surgical article 10 and method of managing surgical articles that comprise various tags in PCT Application No. PCT/US2016/057077, filed on Oct. 14, 2016, the disclosure of which is hereby incorporated by reference.

The surgical article may comprise a surgical sponge 10 comprising an absorbent material body 11. The absorbent material body 11 of the surgical sponge 10 may comprise a top surface 12 and an opposing bottom surface 14. The surgical sponge 10 may further comprise a lead, handle or string 16. The lead 16 may comprise a radio opaque marker material that is configured to show up in a medical scan. For example, the lead 16 may comprise a radio opaque marker material configured to show up in an MM image to allow for identification of a surgical sponge 10 that was inadvertently retained within a patient.

It may be important for HCPs to track surgical sponges 10 before, during, and after a surgical procedure to ensure that a surgical sponge 10 is not inadvertently retained or left within a patient. Therefore, as described above, an RFID tag 20 may be utilized to identify the location and number of sponges used in a surgical procedure. An RFID tag 20 may be coupled to the top surface 12 of the absorbent material body 11 proximate to an edge or corner of the surgical sponge 10. While not shown in the Figures, it is contemplated that the RFID tag 20 may be incorporated into the handle, between layers of the absorbent material or other portions of the surgical sponge 10 in any number of ways. For example, the RFID tag 20 can be adhered to or embedded within the handle or coupled to other portions of the surgical sponge 10.

The detecting element of the RFID tag 20 may be used with a multiplex detection system. The RFID tag 20 can include a capacitor and an antenna (not shown), which receives power from the detecting antenna (RFID antenna) of the reader to charge the capacitor of the RFID tag 20. This capacitor becomes the power source for the operation of an unpowered RFID tag 20. The RFID tag 20 can have an integrated circuit, which includes a reading function, a carrier frequency modulating function, and a read-only memory portion with a burned-in code. The integrated circuit and corresponding antenna of the detecting element are encapsulated in an enclosure that is resistant to blood, water, or saline solution. Thus, the RFID tag 20 can withstand repeated sterilization and be attached to other surgical articles, such as metal instruments, which are sterilized and reused multiple times. Depending on the carrier frequency and the type of RFID tag 20, the RFID tag 20 can vary significantly in cost, size, and resistance to shielding by intervening tissue.

One feature provided by RFID based technology is that the RFID tag 20 may enable detecting the location of the surgical sponge 10 in addition to counting or identifying the surgical sponge 10. Thus, certain RFID tags 20 may serve as both detection elements and counting elements. The RFID tag 20 cooperates with the detecting antenna of the reader to both detect the location of the surgical sponge 10 and provide data for determining the unique identification information of the surgical sponge 10. The RFID tags 20 may operate above the MHz range. Exemplary frequencies can include about 13.35 to 14.15 MHz (high frequency), a range from 850 to 950 MHz (ultra-high frequency), or a range of microwave frequencies (i.e., 2.45 to 2.55 GHz). The added bandwidth provided by these RFID tags 20 can increase the probability of detecting and finding the corresponding surgical sponge 10 within the interrogation zone and within a short period of time.

Turning now to FIGS. 2-9, a surgical article management system 100 for detecting, identifying and managing an inventory of surgical objects during a surgical operation is disclosed. The surgical article management system 100 may be configured to maintain a record of the surgical articles 10 used in the procedure in local memory, or in cooperation with a server 116. The scanning device includes an RFID interrogator, illustrated as the hand-held RFID reader 108, in communication with the local memory. The RFID interrogator includes the physical components and the operating software for generating and receiving the radio frequency signals. Among the physical components of the interrogator are the radio controller, including a signal-generating transmitter, a signal receiver, or a transceiver. The scanning device may also include other input and output components, such as, for example, a barcode reader or other optical scanner.

The record of the surgical articles created and maintained by the system may be stored in non-volatile memory housed in the RFID interrogator, in a computing device in communication with the RFID interrogator local to the surgical article management system 100, or else the record may be communicated to a server 116 or other remote computing device in electronic communication with the surgical article management system 100 for storage. At the conclusion of the surgical procedure, the records can be transmitted to a server 116 and matched with patient records, such as electronic medical records, to update the same and provide an indication of which specific surgical articles were used with each patient at which times. The surgical article management device may have a wired or a wireless connection to the server 116 or other remote device. In some alternatives, there may be one or more devices disposed in communication between the surgical article management system 100 and the server 116. In one example, the surgical article management system 100 within an operating room may communicate with an operating room management computer located in the operating room that is in further communication with other medical devices and tools in the operating room. The operating room management computer may communicate information to a router 118 that acts as a gateway to a remote network resource. The server 116 is also connected to the network, and thus the surgical article management system 100 communicates with the server 116 through multiple layers of devices.

Figure 4:
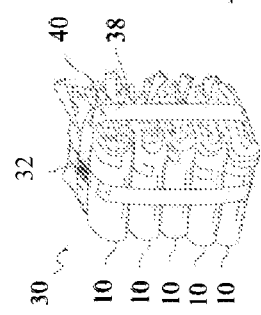
FIG. 4 illustrates an exemplary package of surgical articles in a first configuration.
Figure 5:
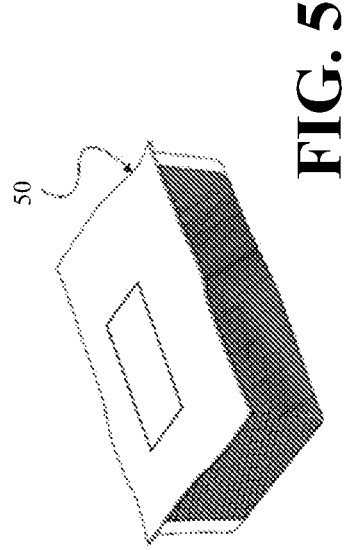
FIG. 5 illustrates an exemplary package of surgical articles in a second configuration.

In FIGS. 4 and 5 examples of various containers for packaging or bundling two or more surgical sponges 10 are shown. A first package 30 is illustrated in FIG. 4 with a strap 38 or plurality of straps 38 used to bundle or package five surgical sponges 10 together. Although illustrated as a package of five sponges 10, it should be appreciated that other numbers of sponges may be packaged together, such as packages of 2, 4, 10 or 20. The strap(s) 38 may be configured to bundle the surgical sponges 10 so as to maintain a defined relationship between the RFID tags 20 of adjacent surgical sponges 10 in the bundle 30. For example, a plurality of surgical sponges 10 may be stacked on top of one another and packaged together by the strap or band 38.

In the alternative package illustrated in FIG. 5, one, or two or more surgical sponges 10 may be packaged or bundled within a pouch or container 50. The container 50 may be similarly configured to the strap, wherein the container 50 maintains a defined relationship between the RFID tags 20 of adjacent surgical sponges 10 in the container 50. The container 50 may comprise a polyTyvek® pouch, a rigid base with a polyTyvek® cover, or similar containment apparatus. Any number of surgical sponges 10, or surgical instruments may be packaged or bundled by the strap 38 or within the container 50.

Figure 2:
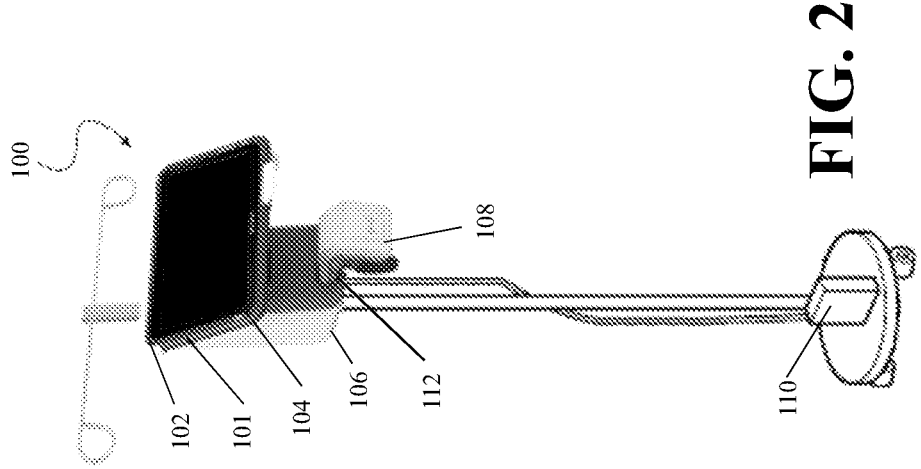
FIG. 2 illustrates an exemplary surgical article management system including a hand-held RFID reader received in a docking cradle.
Figure 6:
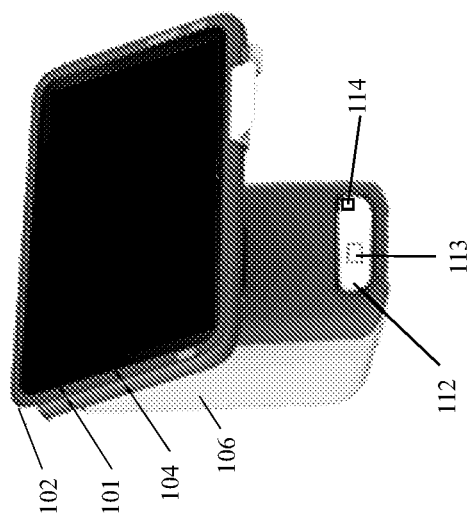
FIG. 6 illustrates a base, system computer and display device of an exemplary surgical article management system where the hand-held RFID reader is removed from the docking cradle.

The surgical article management system 100 illustrated in FIG. 2 includes the hardware and software to communicate with RFID-tagged surgical articles, create and maintain database records managing an inventory of the surgical articles, including identifying type number, type, and unique identification of those surgical articles made available for use in a particular surgical procedure. The system 100 also provides information, alerts, and other responsive actions according to specific rules incorporated in the software for operating the hardware as described in more detail below. The system 100 provides the interface for an HCP to enter information into the database, and to access that information and other information in the database before, during and after a surgical operation. The system 100 provides the communication hardware, protocols, and interface to automatically, or allow an HCP to, direct the communication of the stored information to a remote computing resource, such as a server 116.

In one exemplary configuration, as illustrated in FIG. 2, the system 100 includes a system computer 101 in communication with a display device 102. The display device 102 and the system computer 101 may be an integrated unit, such as a laptop or tablet computer that further includes a touchscreen 104, or other input hardware (not shown). In other alternatives the display device 102 may simply be a monitor in communication with but separate from the system computer 101 as a desktop-type computer. User input functionality may be provided by other hardware in communication with the system computer 101 and the display device 102. Other input hardware (not shown) may include a microphone for voice command control, or a video camera or other sensor to provide gesture control. Further, alternative input hardware may include a trackball, touchpad, keyboard, mouse, or the like.

The display device 102 and system computer 101 may be supported on a base 106. The base 106 may be pole or pedestal mounted, as illustrated in FIG. 2, including a wheeled support making it mobile. In other alternatives, the base 106 may be a mobile cart, or a stationary, wall mounted unit. The base 106 in other alternatives may be supported by or on other equipment present in an operating room environment. The base 106 may be a mechanical support for the display 102 as an integrated display including the power source, computing and input functionality all in the display itself, such as a tablet computer. Alternatively, the base 106 may support functions that are not integrated within the display device 102. For example, the base 106 may house or support the system computer 101, and a rechargeable battery to provide power to the system 100, including providing power to the display device 102. The base 106 may house a central processing unit, memory device, data storage device, other hardware for or in communication with the system computer 101.

The base 106 may also support a hand-held RFID reader 108 in communication with the system computer 101. The RFID reader 108 may be removable and operate remotely from the base 106. The base 106 may provide a dock or cradle 112 for a removeable, mobile RFID reader, such as the hand-held RFID reader 108. When received in the cradle 112, the RFID reader may rely on a power source external to itself and may use wired connections for communication with the system computer 101. Where the hand-held RFID reader 108 is battery operated, the cradle 112 may include a battery charger connection to charge the battery of the hand-held RFID reader 108 when the hand-held RFID reader 108 is received in the cradle 112. Although described as a mobile or hand-held reader, the hand-held RFID reader 108 may be operable while received in the cradle 112.

In one alternative, both the hand-held RFID reader 108 and the system computer 101 housed or supported by the base 106 may be configured for Bluetooth and near field communication (NFC) to facilitate the wireless data communication between the hand-held RFID reader 108 and the system computer 101. Establishing a Bluetooth communication protocol between two devices typically requires the user to enter a code or to perform a confirmation action to ensure that the desired communication devices are properly paired. This is important in the healthcare setting where not being able to pair two devices or accidently pairing the wrong device sets may have an adverse impact on the patient care, including, for example by delaying a necessary medical procedure. In order to minimize a potential risk, the pairing process needs to be intuitive and reliable.

The hand-held RFID reader 108 may include a housing 150 defining a handle 152 and including within the housing 150 the electronics (not shown) for operating as an RFID scanner and for communicating with the system computer 101. The hand-held RFID reader 108 may also provide other features for communicating with and/or controlling the system computer 101. For example, the hand-held RFID reader 108 may include a barcode reader or other optical scanner 155 for reading identification data from surgical objects having computer-readable or human-readable printed tags.

Also included in the housing 150 is a passive NFC tag 154. The cradle 112 includes an NFC reader system 113 in communication with the system computer 101, for example through a USB connection. The passive NFC tag 154 in the hand-held RFID reader 108 has encoded within its memory the Bluetooth address assigned to the reader 108. When the hand-held RFID reader 108 is received in the cradle 112, the NFC reader system 113 of the cradle 112 communicates with the NFC tag 154 inside the hand-held RFID reader 108 and learns the Bluetooth address of the hand-held RFID reader 108 placed within the cradle 112. The NFC devices 113, 154 require a close proximity between components in order to communicate. This required proximity may be a separation distance between the NFC tag 154 and the NFC reader system 113, for example, of about 4 centimeters or less. The NFC reader system 113 in the cradle 112 provides the Bluetooth address of the hand-held RFID reader 108 placed within the cradle 112 to the system computer 101 to be used for pairing the system computer with the correct hand-held RFID reader 108. In an environment with multiple surgical article management systems, each having its own hand-held RFID reader and system computer, this process ensures that the correct pairing is established between the specific RFID reader and the corresponding system computer.

The pairing process may be initiated manually by selecting the operation through a user input on the system computer 101. Alternatively, this process may happen automatically upon the occurrence of a particular event. For example, the system computer 101 may initiate the Bluetooth connection process upon a determination that a hand-held RFID reader 108 has been inserted into the cradle 112, as described in more detail below. Upon this determination, the NFC reader 113 reads the NFC tag 154 of the hand-held RFID reader 108 inserted in the cradle 112 and communicates the received Bluetooth address to the system computer 101. The system computer 101 sends a connection request to the received Bluetooth address, and the hand-held RFID reader 108 accepts the Bluetooth connection request and is thereby paired with the system computer 101.

In some situations, a hand-held RFID scanner 108 is inserted into a cradle 112 where the system computer 101 has an active Bluetooth connection with a hand-held RFID scanner 108. The system computer 101 receives a Bluetooth address from the NFC reader of the cradle 112 and may perform a verification check to ensure that the proper hand-held RFID scanner 108 is received in the cradle 112. In the verification check, the system computer 101 compares the received Bluetooth address from the NFC reader with the Bluetooth address of the active connection. If the two Bluetooth addresses match, the verification check passes, and normal operation is maintained. If the two Bluetooth addresses do not match, the verification fails.

If the verification check fails, the system computer 101 may initiate an alert to the user or take another action. For example, if initiating an alert, the system computer 101 may sound an audible tone; temporarily display a warning on the display device 102; display a warning prompt to the user and require a user input to dismiss the warning; activate a tactile alert in the reader 108; provide some other type of alert; or combinations thereof. Alternatively, the system computer 101 may terminate the active Bluetooth connection and initiate a Bluetooth pairing with the Bluetooth address received from the NFC reader upon the insertion of the hand-held RFID reader 108. In a further alternative, the system computer 101 may notify the user that the active Bluetooth connection does not match the hand-held RFID reader 108 received in the cradle 112 and prompt the user to select whether to maintain the existing active Bluetooth connection or else terminate the active pairing and initiate a new Bluetooth connection with hand-held RFID reader 108 present in the cradle 112.

In other situations, the hand-held RFID reader 108 may be received in the cradle 112 while having an active Bluetooth pairing to a different system computer (i.e., not the system computer 101 which is in communication with the cradle 112 where the hand-held RFID reader 108 is received). In this instance, the system computer 101 may initiate an alert to the user or take another action. For example, if initiating an alert, the system computer 101 may sound an audible tone; temporarily display a warning on the display device 102; display a warning prompt to the user and require a user input to dismiss the warning; activate a tactile alert in the reader 108; provide some other type of alert; or combinations thereof. Alternatively, the system computer 101 may force a disconnection by issuing a disconnect command and then pair the system computer 101 with the hand-held RFID reader 108 present in the cradle 112.

The cradle 112 may determine whether the hand-held RFID reader 108 is present within the cradle 112. The determination may use the NFC reader system 113 of the cradle 112 to act as a presence sensor by periodically attempting to read the passive NFC tag 154 of hand-held RFID reader 108 on a continuous cycle. If the hand-held RFID reader 108 is docked, the NFC reader 113 in the cradle 112 will detect and read the passive NFC tag 154, and if the hand-held RFID reader 108 is not docked, the NFC reader 113 in the cradle 112 will not detect or read an NFC tag. The system computer 101 may request the presence status of the hand-held RFID reader 108 at a rate that is equal to or less than the read cycle rate of the NFC reader system 113 in the cradle 112.

In other alternatives, the cradle 112 may be instrumented with a sensor or a switch 114, separate from the NFC communication, toggled by the presence of the hand-held RFID reader 108 to determine whether the hand-held RFID reader 108 is present within the cradle 112. The cradle 112 may include a sensor as switch 114 disposed within or adjacent to the cradle 112 in which the hand-held reader 108 is received when in the docked configuration. The switch 114 may take one or more of a variety of forms described in more detail below. In each case, the switch 114 can communicate its status to the surgical article management system 100, either by generating a signal reflecting its status, responding to an interrogating signal, or otherwise. For example, in some configurations, the switch 114 may open or close an electric circuit depending on its actuation.

The switch 114 is in communication, directly or indirectly, with the system computer 101 to communicate its status to, or to have its status read by, the system computer 101. As described above, the system computer 101 may be a tablet computer, or it may be integrated into base 106 or the hand-held RFID reader 108. In any case, the switch 114 is in wired or wireless communication with the system computer 101. Accordingly, the switch 114 may include a processor, memory, and communication hardware and programming for the specific implementation to accomplish the communication with the system computer 101.

The switch 114 may include a physical switch positionable in at least two positions, a first position when the reader is removed from the cradle and a second position when the reader 108 is received in the cradle 112. Disposing the hand-held reader 108 in the cradle 112, the housing of the reader 108 in the cradle 112 may toggle the switch from the first position to the second position. The switch 114 in the form of a physical switch may further include a spring or other biasing element urging the switch toward the first position so that removal of the hand-held reader 108 automatically displaces the switch from the second position to the first position. In one position, the switch closes a circuit which can be read by the system computer 101 in determining the presence of the hand-held RFID reader 108 in the cradle 112. In the other position, the switch opens the circuit read by the system computer 101 in determining the absence of the hand-held RFID reader 108 from the cradle 112.

The switch 114 may take other forms besides a physical toggle switch. In one example, the switch 114 may be a photoelectric or optoelectronic switch actuated upon a difference in light or electromagnetic radiant energy incident on the switch 114. The switch 114 in this form may be calibrated to a first energy level when the reader is removed from the cradle and a second energy level when the reader is received in the cradle 112. The switch 114 in this form may generate a signal and communicate the signal to the system computer 101. The signal generated can signify the amount of energy received at the switch 114 and the system computer 101 may be programmed to evaluate the amount of energy at the switch corresponding to the presence or absence of the hand-held reader 108 in the cradle 112.

The switch 114 may be integrated into a wired communication between the hand-held RFID reader 108 and the cradle 112. In one example, the hand-held RFID reader 108 and the cradle 112 may include complementary connectors for electronic communication such that when the hand-held RFID reader 108 is received in the cradle 112 the connectors are in engagement and allow communication between the hand-held RFID reader 108 and the cradle 112. When the hand-held RFID reader 108 is not present in the cradle 112, the connectors are not in engagement and do not allow communication between the hand-held RFID reader 108 and the cradle 112. The communication between the cradle 112 and the hand-held RFID reader 108 may be relayed to or evaluated by the system computer 101 in a determination of the presence or absence of the hand-held RFID reader 108 in the cradle 112.

The switch 114 may be integrated into a power charging function of the cradle 112 providing battery recharging to the hand-held RFID reader 108. The cradle 112 may provide battery charging to the hand-held RFID reader 108 when the hand-held RFID reader 108 is received in the cradle 112. The cradle 112 may include oversight circuitry to measure, monitor, record, and store data representing the power, voltage, current, or other parameter of the battery recharging operation. The switch 114 may be implemented in connection with this oversight circuitry so that the determination of the presence of the hand-held RFID reader 108 is dependent on the status of the power charging operation. That is, the system computer 101 may determine that the hand-held RFID reader 108 is present in the cradle 112 when the hand-held RFID reader 108 is receiving power from the cradle 112.

The RFID reader 108 may include an RFID transceiver enabling communication between the RFID reader 108 and an RFID tag, such as tag 20 of surgical sponge 10. The RFID reader 108 may include its own power source, data processing, and memory or data storage devices internal to the RFID reader 108. The RFID reader 108 may be configurable to operate with varying levels of power provided to the RFID transceiver to change the effective output of radio energy from the antenna.

The system 100 may include or be in communication with an external computing device 110. This external device 110 may include additional memory or data storage. The external device 110 may provide wireless connectivity of other systems, such as a router 118 or modem to communicate with remote resources, such as a hospital network or internet server 116. In other alternatives, network connectivity is integrated into the system computer 101 without the need for an external device 110.

The system 100 may be provided within a surgical environment such as a hospital operating room. The system 100 may be adapted to be draped for positioning in the sterile field. Alternatively, the system 100 may be positioned adjacent to but outside of the sterile field to avoid the need for sterile draping. In further alternatives, the base 106 may be positioned outside of the sterile field, but the mobile hand-held RFID reader 108 may be separate from the base 106 and enter the sterile field with appropriate sterile draping or other sterilization-maintaining measures as may be known in the art.

Figure 3:
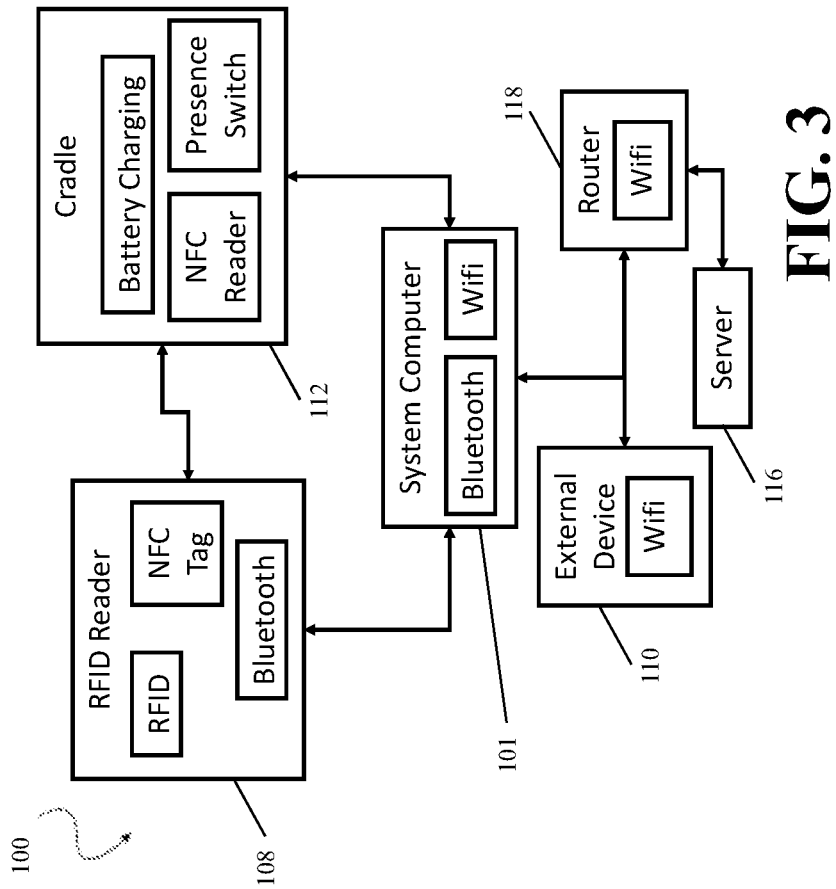
FIG. 3 illustrates a schematic of the surgical article management system showing the exemplary lines of communication between the different devices.

Referring now to FIG. 3, a schematic representation of the system 100 is provided, illustrating exemplary lines of communication between the components in one configuration. The system computer 101 is in data communication with the hand-held RFID reader 108, and the cradle 112. The system computer 101 may also be in data communication with the external computer device 110, a router 118, a server 116, or combinations thereof. The system computer 101 and the hand-held RFID reader both include Bluetooth radios, antennas, and drivers for bi-directional data communication using the Bluetooth protocols. The system computer 101 is in data communication with the cradle 112, for example through a wired connection, such as a USB connection. Alternatively, the system computer 101 and the cradle 112 may be in other wired or wireless communication, directly or indirectly, through one or more additional intermediary devices, for example, through a Wi-Fi router or USB hub. The system computer 101 may be in wired or wireless communication, directly or indirectly, through one or more additional intermediary devices, with the external device 110, the server 116, or combinations thereof, via Wi-Fi, or other communication protocol.

The hand-held RFID reader 108 is in communication with the cradle 112 when the hand-held RFID reader 108 is received in the cradle 112. As described above, the hand-held RFID reader 108 and the cradle 112 are equipped with the NFC tag 152 and the NFC reader 113, respectively. In addition, the hand-held RFID reader 108 and the cradle 112 may be in communication via battery charging, or other wired communication, for exchanging data between the cradle 112 and the hand-held RFID reader 108. In one configuration, the hand-held RFID reader 108 communicates with the system computer 101 via a wired connection between the hand-held RFID reader 108 and the cradle 112, with the cradle 112 acting as a gateway device between the hand-held RFID reader 108 and the cradle 112.

Figure 9:
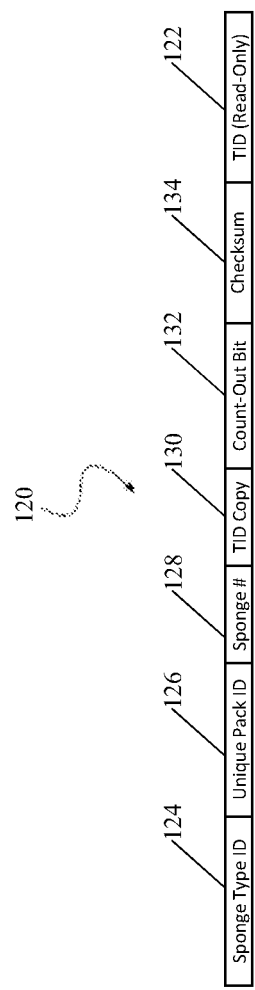
FIG. 9 illustrates an identification scheme of information stored on an article RFID tag.

Referring now to FIG. 9, an exemplary identification scheme 120 that may be stored in the RFID tag 20 is shown. Each of the surgical articles, e.g., surgical sponges 10, are tagged with an RFID tag, e.g., tag 20, containing data to uniquely identify the individual item as well as provide other information relevant to manage an inventory of surgical articles. A variety of tags and data encoding schemes are presently available and the description of the identification scheme 120 is not intended to be limiting. Generally, RFID tags will be manufactured with a tag identification (TID) 122 assigned by the manufacturer of the RFID integrated circuit (IC). This TID 122 is typically stored in a write-once memory location, otherwise known as a read-only memory location on the IC. In addition to the TID 122 provided by the tag manufacturer, other information may be provided in connection with associating the tag IC to a particular surgical article, such as surgical sponge 10.

The identification scheme 120 may include a portion 124 dedicated to identifying the type of surgical article to which the tag is affixed, i.e., sponge type ID. In one alternative, the sponge type ID 124, as described above is a value which may be used by the system computer 101 in combination with a look-up table to retrieve further specification information relevant to the sponge type, such as quantity of sponges for that sponge type, name to be displayed on the user-interface, and others. The look-up table may be stored local to the system computer 101, such as in data storage of an integrated display device 102, data storage provided in the base 106, data storage of an external computer device 110, or remotely from the system computer 101, such as on a hospital network or internet server location. In other alternatives, the sponge type ID 124 may be encoded to provide certain information directly, rather than requiring correlation to a look-up table value.

The identification scheme 120 may include information serving to identify the package of sponges, how many sponges are in a package and where a particular sponge falls within that quantity. For example, the identification scheme may include a unique package ID 126 and a sponge number 128. Each package of sponges may be assigned a unique identification that will be shared by all members common to a single package. The unique package ID 126 may also be encoded such that certain values within the unique package ID serve to identify or designate the package as being of a particular type of surgical article. The unique package ID 126 may also be encoded such that certain values identify the quantity of sponges within the package. For each sponge 10 in a package, the sponge number 128 differentiates it from the other sponges in the package. For example, in a package of ten sponges 10, there is one sponge with sponge number 128 of 1, one sponge with 2, and so on up to sponge number 128 of 10. Together, the unique package ID 126 and the sponge number 128 may represent package content information stored on the tag.

The identification scheme 120 may include a copy 130 of the read-only TID in the rewritable memory as a security measure to ensure that the written data has been uniquely assigned and not copied from a previous tag. The TID copy 130, either alone, or in combination with other data stored on the tag may serve as a unique identifier to uniquely identify the sponge to which the tag is affixed. As a further potential security measure, or a way to ensure that the data has not been corrupted, in the identification scheme 120 is the checksum 134. All or a portion of the data contained in the identification scheme on a tag 20 may be used as an input for a mathematical algorithm to generate a checksum value. The particular mathematical algorithm may be proprietary to the sponge manufacturer to ensure that its tags are uniquely identifying only first-party produced sponges, or sponges produced by an otherwise authorized party. A simple example of such an algorithm may be to sum all the values in the other data fields of the identification scheme 120, divide the sum by a given constant, and use the remainder as the checksum value. Without knowing the particular constant used in the algorithm, unauthorized products may be detected by the system computer 101 as a step of the count-in process where the tag data is verified for authenticity.

The identification scheme 120 may include a provision to write to the tag in the course of the count-in or count-out process. For example, identification scheme 120 in FIG. 3 includes the count-out bit 132 which is a flag that is toggled after a sponge has been counted-out. This toggle may be accomplished, for example, by sending instructions from the RFID reader operating in a count-out mode instructing the tag to change the value of this data field upon being counted-out at a conclusion of a surgical procedure. This value may be particularly advantageous in an emergency situation where RFID-tagged sponges are used with a patient without completing the normal count-in procedure. The count-out bit 132 is a value toggled during the process and may be used by the system computer 101 in correctly managing the inventory of surgical articles during a surgical procedure.

The system 100 manages the inventory of surgical articles during a surgical procedure based on the information stored on the RFID tags of the surgical articles, such as surgical sponges 10 and RFID tags 20. The system 100 may include a database of records storing information necessary to manage the inventory of surgical articles, specifically identifying the counted-in and counted-out status of surgical articles associated with particular surgical procedures. In particular, the system 100 may be configured to count-in the surgical articles at the beginning of a surgical procedure by scanning the articles with the RFID reader 108, and to count-out the surgical articles at the end of the procedure. To overcome the challenges of ensuring the proper counting in and counting out of sponges, the hand-held RFID reader 108 operation may be restricted based on the determination of its presence or its absence from the cradle 112. The hand-held RFID reader 108 may be operable to both count-in and count-out the surgical articles and may be set to operate in only one mode at a time.

The user may input a selection to operate the hand-held RFID reader 108 in either the count-in or the count-out mode. The system computer 101 may display a selection on the display device 102 prompting the input of the user to select one of the count-in or the count-out mode. The user may input the selection through the touchscreen 104 or other input device in communication with the system computer 101. In one alternative, the hand-held RFID reader 108 may include a mode selector 156 as a switch or button that can be toggled to select the operating mode of counting-in or counting-out surgical articles on the reader 108 directly. The selection in this alternative can be communicated from the reader 108 to the system computer 101. The system computer 101 may update the display device 102 to reflect the operating mode selected by the user. In other examples, the user may input an operating mode selection via gesture, voice command, keyboard input, or otherwise.

Figure 6A:
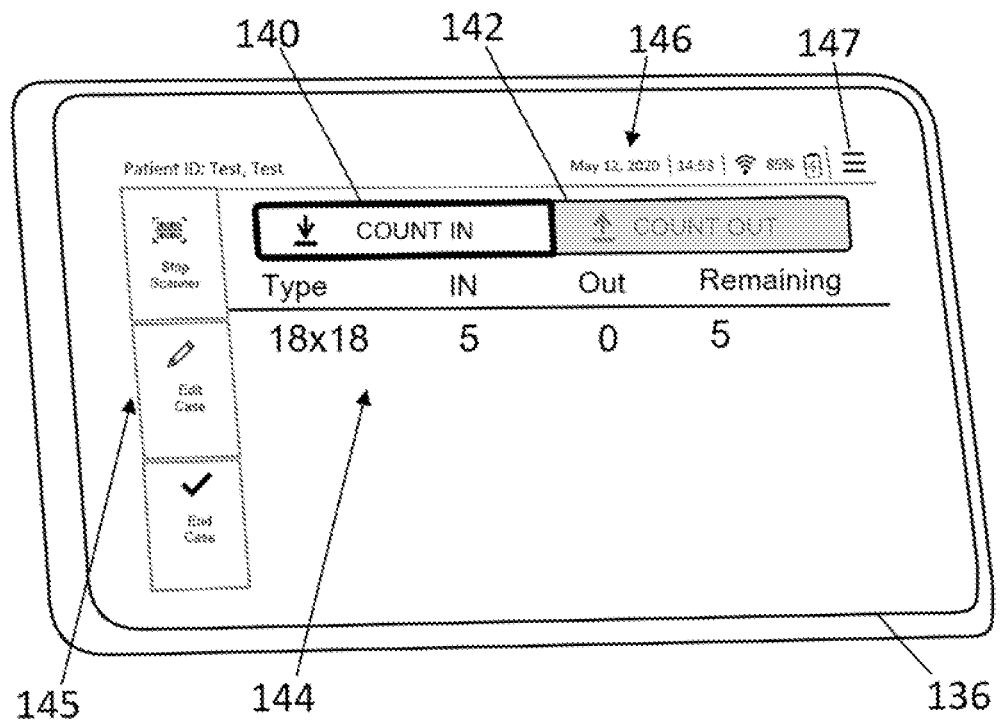
FIG. 6A illustrates an exemplary graphical user interface of the display device with the system operating in the count-in mode.
Figure 6B:
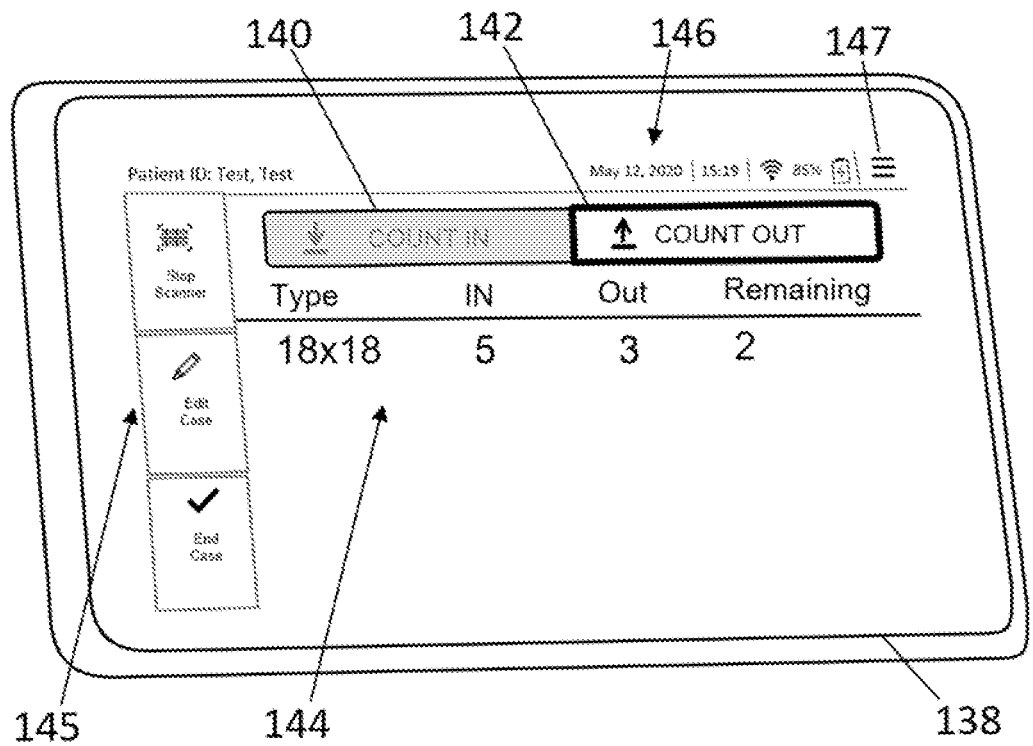
FIG. 6B illustrates an exemplary graphical user interface of the display device with the system operating in the court-out mode.
Figure 8:
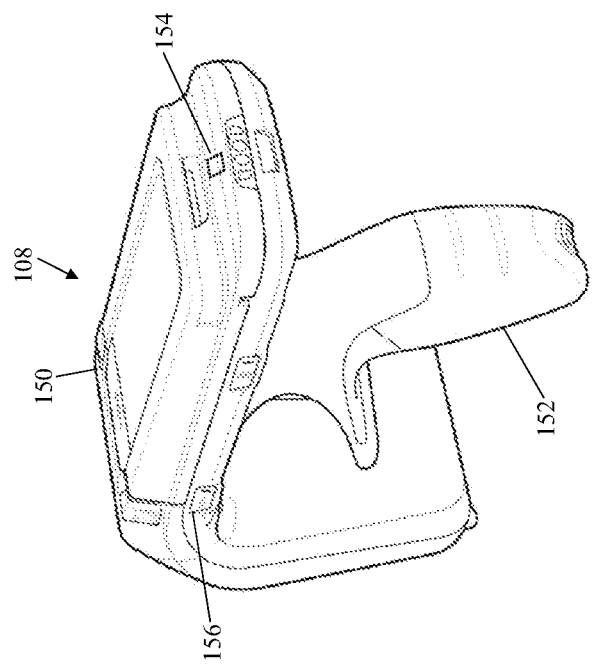
FIG. 8 illustrates an exemplary hand-held RFID reader from a rear perspective view.
Figure 7:
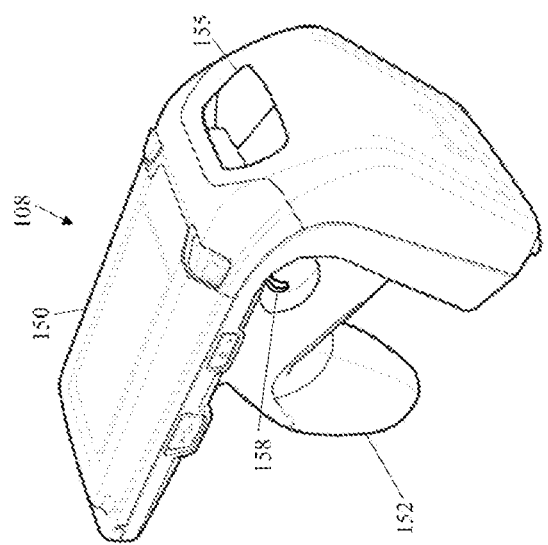
FIG. 7 illustrates an exemplary hand-held RFID reader from a front perspective view.

FIGS. 6A and 6B illustrate exemplary display outputs 136, 138 as graphical user interfaces of the display device 102 in the count-in mode and the count-out mode, respectively. The display output 136 indicates the count-in mode selection 140 as active, while the count-out mode selection 142 is inactive, being greyed out. The display output 138 indicates the count-out mode selection 142 as active, while the count-in mode selection 140 is inactive, being greyed out. The display output 138 further includes a data table section 144 that identifies the surgical articles active in the case. The display output 138 may also include operation selections 145 along, for example, the left border of the display. Additional information 146 about the case, or about the system, may be displayed along a top border of the display output 138. This additional information 146 may include, for example, patient name, system date and time, connectivity status, battery charge and status, combinations thereof or other information not specifically identified. The display output 138 may provide a menu button 147 to access additional functional options of the system 100. The exemplary display outputs 136, 138 are not intended to be limiting and other presentations of the information may be possible without departing from the scope of this description.

While in the count-in mode, the hand-held RFID reader 108 emits an interrogation signal and, based on the response signal or signals received from the surgical articles, identifies the responsive articles as counted-in for use in the surgical procedure. Emitting the interrogation signal in the count-in mode can be done on a continuously repeating cycle persisting while the system is in the count-in mode. Alternatively, the interrogation signal may be emitted upon an input from the user. In one example, the hand-held RFID reader 108 may include a handle 152 having a trigger 158 that when depressed by the user causes the reader 108 to emit an interrogation signal for a limited period of time or until a responsive signal is received within that limited time. After the limited period of time or a receipt of a response, the reader 108 may then reset to be ready for the next check-in interrogation cycle. In another example, the hand-held RFID reader 108 may initiate a count-in interrogation cycle by the press of a button, a gesture input, a voice command, or other input from the user. As illustrated in the exemplary display output 138, shown in FIG. 6A, the data table section 144 identifies the surgical articles that have been counted-in to the surgical procedure. In the illustrated example, one set of five 18 inch by 18 inch surgical sponges has been counted-in for use in the procedure.

The hand-held RFID reader 108 is in communication with the system computer 101 and stores data as a record of the surgical articles identified as counted-in for use in the surgical procedure. In response to the interrogation signal while in the count-in mode, the hand-held RFID reader receives a responsive signal comprising data to identify the responsive surgical article. As described above, this data may be encoded on the article RFID tag to include a unique identifier for the surgical article, identification of the type of article, identification of other co-packaged articles, other information about the article, and combinations thereof. The reader 108 may be further configured to limit the count-in operation. In one example, the reader 108 may be configured to require a responsive signal for each article within a multi-article package before any of the articles are identified as counted-in. In another example, the reader 108 in combination with the system computer 101 may be provided with an inventory list of articles allocated to the particular surgical operation for which the count-in process is being performed and may perform a check of the responsive signal against the inventory list to ensure the article identified by the responsive signal is present in the inventory list. In yet another example, for certain types of articles that are reusable, the reader 108 in combination with the system computer 101 may perform an additional check to ensure that the article is not re-used beyond its limited number of reuses, or is scheduled for preventative maintenance, or the like. Additional description of the count-in functionality has been provided by the Applicant in Application No. 62/894, 300, filed Aug. 30, 2019, the entirety of which is incorporated by reference.

While in the count-out mode, the hand-held RFID reader again emits an interrogation signal and, based on the responsive signal or signals received from the surgical articles, identifies the responsive articles as counted-out for having been counted-in but now being removed from use in the surgical procedure. The surgical articles may have been used in the surgical procedure and thereafter removed from the patient to be counted-out. Or, the surgical articles may have been counted-in, made available for use in the surgical procedure, but ultimately not used for the procedure. The counted-in but not used articles still require counting-out to close the surgical procedure and ensure that no surgical articles are inadvertently left in the patient following the surgical procedure. As illustrated in the exemplary display output 138, shown in FIG. 6B, the data table section 144 identifies the surgical articles that have been counted-in to the surgical procedure, and identifies how many have been counted-out, and the difference as the number remaining. In the illustrated example, one set of five 18 inch by 18 inch surgical sponges has been counted-in for use in the procedure, three of which have been counted out and two that remain counted-in and which have not yet been counted out.

Counting-in surgical articles for use in the surgical procedure may be performed with the hand-held RFID reader 108 when docked in the cradle 112, when used remote from the base 106, or when removed from the cradle 112. Prior to the surgical procedure, the inventory of surgical articles allotted for the procedure may be laid out or arranged on a table. The hand-held RFID reader 108 may be brought to the arranged surgical articles and scanned-in in a quick and efficient manner in this way, avoiding the need to lift and present the articles individually to the reader 108 when docked in the cradle 112 on the base 106. The system computer 101 may allow the reader 108 to operate in the count-in mode either received in the cradle 112 or used remotely from the cradle 112.

To avoid unintentional or accidental counting-out of articles from the surgical procedure prematurely, the surgical article management system 100 may be restricted from operating in the count-out mode when the reader 108 is removed from the cradle 112. The system computer 101 may prohibit the user from selecting the count-out operating mode and prevent the system from identifying counted-in surgical articles as being counted-out from the surgical procedure. The system computer 101 may receive a signal or monitor the condition of a switch 114, depending on the specific implementation as discussed above, to permit or restrict the user's selection of the count-out mode.

In one alternative, the system computer 101 enables operation of the reader 108 in the count-out mode based on the cradle 112 determining the hand-held reader 108 is present in the cradle 112. The cradle 112 determines the presence of the reader 108 based on the status of the switch 114, or by NFC communication between the reader 108 and the cradle 112. The system computer 101 may disable the user input that allows the user to select operation in the count-out mode while the reader 108 is removed from the cradle 112. This may include greying out the count-out mode selection button displayed on the display device 102 with a touchscreen input, such as is illustrated in FIG. 6A. Alternatively, the system computer 101 may otherwise indicate that the count-out mode selection 142 is unavailable to distinguish between the count-out mode being merely inactive and being unavailable for selection. For example, the system computer may strikethrough or X-out the count-out mode selection button 142, or may use different color schemes (not shown).

The system computer 101 may be further configured to initiate an alert if the user attempts to toggle the reader 108 into the count-out mode while the reader 108 is removed from the cradle 112. For example, the system computer 101 may sound an audible tone; temporarily display a warning on the display device 102; display a warning prompt to the user and requiring user input to dismiss the warning; activate a tactile alert in the reader 108; provide some other type of alert; or combinations thereof. In some alternatives, the system computer 101 may allow the user to override the limitation and allow the user to force the reader 108 to operate in the count-out mode even while removed from the cradle 112. The system computer 101 may be programmed to require the user to input a series of commands, selections, and confirmations in order to override the operating mode restriction to force the reader 108 to operate in the count-out mode while removed from the cradle 112.

The hand-held RFID reader 108 may be operated in the count-out mode while received in the cradle 112 and thereafter removed from the cradle 112. The system computer 101 in combination with the cradle 112 and the reader 108 may monitor the continued presence of the reader 108 in the cradle 112 and initiate an alert if the reader 108 is removed from the cradle 112 while in the count-out mode. For example, the system computer 101 may disable the reader 108 from further operation in the count-out mode upon its removal from the cradle 112. The system computer 101 may also sound an audible tone; temporarily display a warning on the display device 102; display a warning prompt to the user and require user input to dismiss the warning; activate a tactile alert in the reader 108; provide some other type of alert; or combinations thereof upon the determination that the reader 108 is removed from the cradle 112 while in the count-out mode. In some alternatives, the system computer 101 may allow the user to override the limitation and allow the user to force the reader 108 to operate in the count-out mode even while removed from the cradle 112. The system computer 101 may be programmed to require the user to input a series of commands, selections, and confirmations in order to override the operating mode restriction to force the reader 108 to operate in the count-out mode when the system computer 101 detects that the reader 108 has been removed from the cradle 112.

Figure 10:
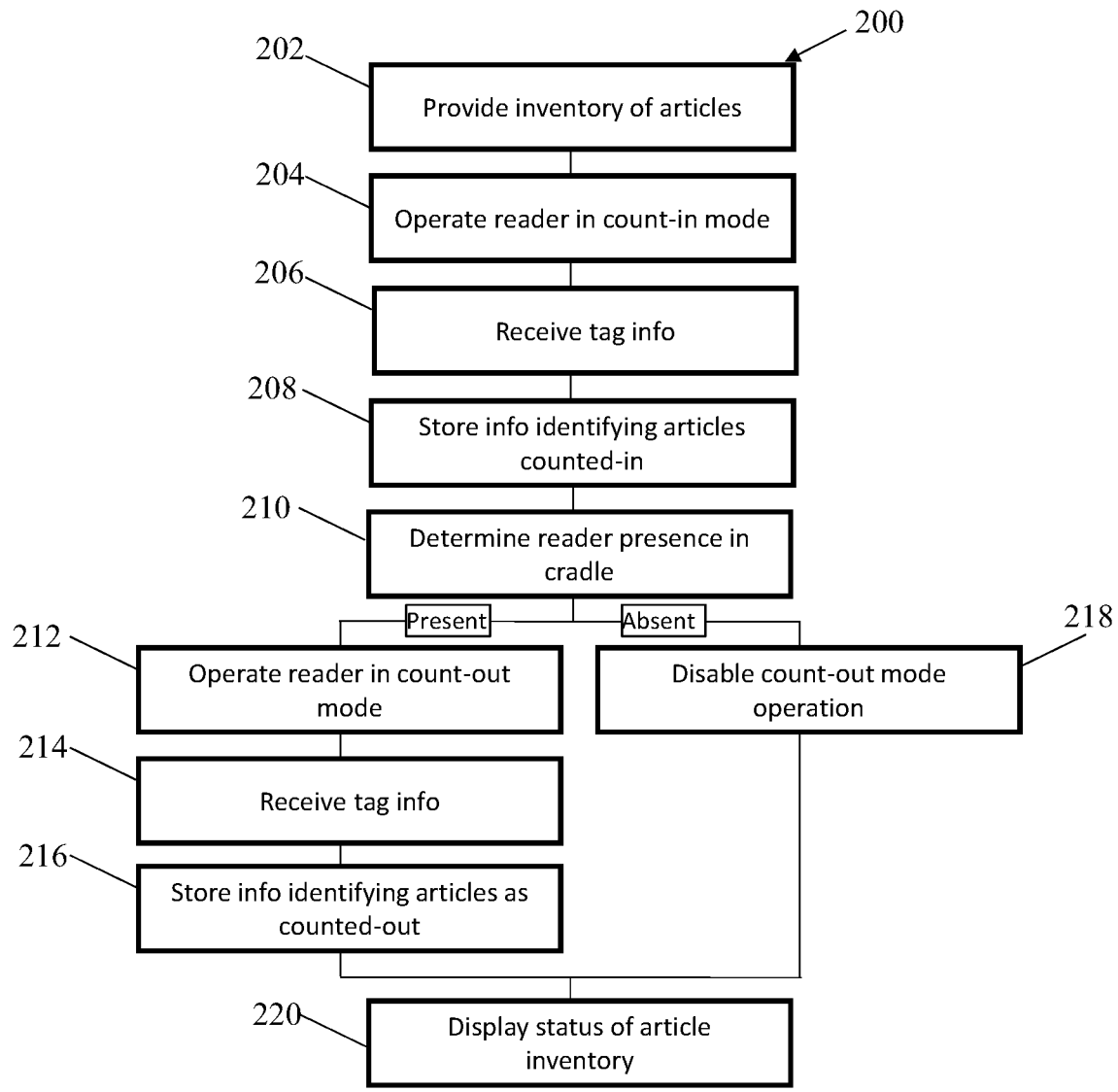
FIG. 10 illustrates one method of using the disclosed surgical article management system.

In accordance with the description of the system components and operation above, a first method 200, illustrated in FIG. 10, is provided for ensuring the proper removal of surgical articles following a surgical procedure. The method may include providing at 202 an inventory of surgical articles, where each surgical article includes an identification tag including identification information uniquely identifying the surgical article. The method includes at 204 operating a hand-held RFID reader in a first operating mode for counting-in surgical articles to a surgical procedure. Operating the hand-held RFID reader in the first operating mode includes at 206 receiving the information from the identification tag included with each surgical article and at 208 storing information uniquely identifying the surgical articles as counted-in for use in the surgical procedure. The method includes at 210 determining whether the reader is present in the cradle. The method includes at 212 operating the hand-held RFID reader in a second count-out mode for counting-out surgical articles from the surgical procedure. Operating the hand-held RFID reader in the second operating mode includes at 214 receiving tag information and at 216 storing information uniquely identifying the surgical articles as counted-out and removed from the surgical procedure. The method may include placing the hand-held RFID reader in a cradle if it were removed from the cradle if used remotely for counting-in surgical articles. The cradle is operable to determine whether the hand-held RFID reader is present in the cradle or removed from the cradle. The method further includes at 212 operating the hand-held RFID reader in the second count-out mode only when the cradle determines that the hand-held RFID reader is present in the cradle, and at 218 disabling operation of the hand-held RFID reader in the second count-out mode when the cradle determines that the hand-held RFID reader is absent from the cradle.

In one example of the method, the cradle is operable to determine the presence or absence of the hand-held RFID reader via NFC or wireless communication technology between the cradle and the hand-held RFID reader. In one example, the cradle is operable to determine the presence or absence of the hand-held RFID reader via one of a physical switch, a photoelectric switch, an optoelectronic switch, or combinations thereof. In one example, the cradle is operable to determine the presence or absence of the hand-held RFID reader based on one of wired communication between the hand-held RFID reader and the cradle; active power transfer between the cradle and the hand-held RFID reader in a battery recharging operation; or combinations thereof.

The method may include the step of selecting, on a base unit, from among the first count-in mode and the second count-out mode for the hand-held RFID reader operation. In one example, the base unit comprises a display device and the selection on the base unit includes providing input via a touchscreen in communication with the base unit. The method may include at 220 displaying, on the display device, a status of the article inventory, including a number or identification of articles counted-in, a number or identification of articles counted-out and combinations thereof. The method may include displaying, on the display device, a status of the hand-held RFID reader as operating in the first count-in mode or in the second count-out mode.

Several descriptions have been discussed in the foregoing disclosure. However, the discussions herein are not intended to be exhaustive or limit any particular form. The terminology which has been used is intended to be in the nature of words of description rather than of limitation. Many modifications and variations are possible in light of the above teachings and the disclosure may be practiced otherwise than as specifically described.

What is claimed is:

1. A surgical article system for managing removal of surgical articles following a surgical procedure, the surgical articles each including an identification tag comprising identification information identifying the corresponding surgical article, the system comprising:

a hand-held reader operable to read the identification information from the identification tags;

a cradle, the cradle adapted to receive the hand-held reader;
at least one processor; and
a non-transitory computer readable memory storing a set of instructions that when executed by the at least one processor causes the system to:
selectively operate the hand-held reader in a first count-in mode wherein the system stores information, based on the identification information, identifying the surgical articles as counted-in for use in the surgical procedure; and
selectively operate the hand-held reader in a second count-out mode wherein the system stores information, based on the identification information, identifying the surgical articles as counted-out and removed from the surgical procedure,
wherein the cradle is operable to determine a presence of the hand-held reader received in the cradle,
wherein the system enables an operation of the hand-held reader in the second count-out mode based on the presence of the hand-held reader received in the cradle,
wherein the system further comprises a user interface for receiving a user selection to operate the hand-held reader in the second count-out mode, and
wherein the set of instructions when executed by the at least one processor further causes the system to:
responsive to the user interface receiving the user selection to operate the hand-held reader in the second count-out mode when the hand-held reader is not present in the cradle, trigger an alert without triggering the hand-held reader to operate in the second count-out mode; and
responsive to the user interface receiving a user selection of an override option after the alert is triggered, trigger an operation of the hand-held reader in the second count-out mode.

2. The system of claim 1, wherein the surgical articles are surgical sponges.

3. The system of claim 1, wherein the hand-held reader comprises an RFID reader and wherein each identification tag comprises an RFID tag.

4. The system of claim 1, wherein the hand-held reader comprises the at least one processor and the non-transitory computer readable memory storing the set of instructions.

5. The system of claim 4, wherein the hand-held reader further comprises a display device and an input device, and wherein the set of instructions when executed by the at least one processor further causes the system to display on the display device a status of the hand-held reader selectively operated in the first count-in mode or the second count-out mode.

6. The system of claim 5, wherein the set of instructions when executed by the at least one processor further causes the system to display information selected from among the identification information of the surgical articles, a count of surgical articles identified as counted-in, a count of surgical articles identified as counted-out, and combinations thereof.

7. The system of claim 1, further comprising a base unit in electronic communication with the hand-held reader, the base unit comprising the at least one processor, the non-transitory memory storing the set of instructions, a display device, and an input device; and wherein the set of instructions when executed by the at least one processor further causes the system to display on the display device a status of the hand-held reader selectively operated in the first count-in mode or the second count-out mode.

8. The system of claim 7, wherein the set of instructions when executed by the at least one processor further causes the system to display information selected from among the identification information of the surgical articles, a count of surgical articles identified as counted-in, a count of surgical articles identified as counted-out, and combinations thereof.

9. The system of claim 7, wherein the base unit is a tablet computing device and the input device is a touchscreen of the tablet computing device.

10. The system of claim 9, further comprising a mobile pedestal stand having a pole, the base unit and the cradle supported on the pole; and the pedestal stand arranged to be disposed outside a sterile field of the surgical procedure.

11. The system of claim 1, wherein the cradle comprises a switch, wherein the hand-held reader, when received by the cradle, actuates the switch, and wherein the cradle is operable to determine the presence of the hand-held reader received in the cradle based on the actuation of the switch.

12. The system of claim 1, wherein the cradle is operable to determine a presence of the hand-held reader received in the cradle via near field communication between the cradle and hand-held reader.

13. The system of claim 12, wherein the near field communication between the cradle and the hand-held reader requires a proximity between the cradle and hand-held reader present only when the reader is received in the cradle.

14. The system of claim 12, further comprising a base unit, the base unit comprising the at least one processor, the non-transitory memory storing the set of instructions, a display device, and an input device; and wherein the base unit is in electronic communication with the hand-held reader via a Bluetooth communication protocol.

15. The system of claim 14, wherein a Bluetooth pairing is made between the base unit and the hand-held reader based on information communicated via the near field communication between the hand-held reader and the cradle.

16. The system of claim 1, wherein the cradle is operable to determine a presence of the hand-held reader repeatedly while the system is selectively operating the hand-held reader in the second count-out mode.

17. The system of claim 16, wherein the set of instructions when executed by the at least one processor further causes the system to trigger an alert and terminate operating the hand-held reader in the second count-out mode based on the cradle determining the hand-held reader is not present in the cradle.

18. A method executed by at least one processor for managing removal of surgical articles following a surgical procedure, the surgical articles each including an identification tag comprising identification information identifying the corresponding surgical article, the method comprising:
operating a hand-held reader in a first count-in mode including storing information identifying the surgical articles as counted-in for use in the surgical procedure;
operating the hand-held reader in a second count-out mode including storing information identifying the surgical articles as counted-out and removed from the surgical procedure;
determining a presence or absence of the hand-held reader in a cradle, wherein operating the hand-held reader in the second count-out mode is based on the determination of the hand-held reader being present in the cradle;
receiving via a user interface a user selection to operate the hand-held reader in the second count-out mode when the hand-held reader is not present in the cradle;

responsive to receiving the user selection to operate the hand-held reader in the second count-out mode when the hand-held reader is not present in the cradle, triggering an alert without triggering the hand-held reader to operate in the second count-out mode;

receiving via the user interface a user selection of an override option after the alert is triggered; and responsive to receiving the user selection of the override option after the alert is triggered, triggering operation of the hand-held reader in the second count-out mode.

19. The method of claim 18, further comprising: determining the hand-held reader has been removed from the cradle; and terminating operation of the hand-held reader in the second count-out mode based on the determination that the hand-held reader has been removed from the cradle.

20. The method of claim 18, wherein the surgical articles are surgical sponges.

\* \* \* \* \*